(12) United States Patent
Boettcher et al.

(10) Patent No.: US 11,464,833 B2
(45) Date of Patent: *Oct. 11, 2022

(54) METHODS FOR TREATING OR PREVENTING TISSUE ADHESIONS

(71) Applicant: NEUTROLIS, INC., Cambridge, MA (US)

(72) Inventors: Michael Boettcher, Hamburg (DE); Tobias Fuchs, Hamburg (DE)

(73) Assignee: NEUTROLIS, INC., Cambridge, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/479,499

(22) PCT Filed: Jan. 22, 2018

(86) PCT No.: PCT/EP2018/051444
§ 371 (c)(1),
(2) Date: Jul. 19, 2019

(87) PCT Pub. No.: WO2018/134403
PCT Pub. Date: Jul. 26, 2018

(65) Prior Publication Data
US 2019/0374620 A1  Dec. 12, 2019

(30) Foreign Application Priority Data
Jan. 20, 2017 (EP) ..................... 17152341

(51) Int. Cl.
*A61K 38/46* (2006.01)
*A61P 41/00* (2006.01)

(52) U.S. Cl.
CPC ............ *A61K 38/465* (2013.01); *A61P 41/00* (2018.01); *C12Y 301/21001* (2013.01)

(58) Field of Classification Search
CPC ........ A61K 38/465; A61P 41/00; A61P 17/02; C12Y 301/21001
See application file for complete search history.

(56) References Cited

U.S. PATENT DOCUMENTS

| | | |
|---|---|---|
| 6,270,989 B1 | 8/2001 | Treco et al. |
| 6,482,626 B2 | 11/2002 | Baker et al. |
| 6,656,685 B2 | 12/2003 | Utermohlen et al. |
| 7,612,032 B2 | 11/2009 | Genkin et al. |
| 8,388,951 B2 | 3/2013 | Genkin et al. |
| 8,431,123 B2 | 4/2013 | Genkin et al. |
| 8,535,663 B2 | 9/2013 | Genkin et al. |
| 8,796,004 B2 | 8/2014 | Genkin et al. |
| 8,916,151 B2 | 12/2014 | Genkin et al. |
| 9,072,733 B2 | 7/2015 | Genkin et al. |
| 9,149,513 B2 | 10/2015 | Bartoov et al. |
| 9,198,957 B2 | 12/2015 | Ratner et al. |
| 9,205,133 B2 | 12/2015 | Dawson et al. |
| 9,248,166 B2 | 2/2016 | Gerkin et al. |
| 9,402,884 B2 | 8/2016 | Burns |
| 9,642,822 B2 | 5/2017 | Wagner et al. |
| 9,770,492 B2 | 9/2017 | Genkin et al. |
| 9,845,461 B2 | 12/2017 | Genkin et al. |
| 9,867,871 B2 | 1/2018 | Jain |
| 10,617,743 B2 | 4/2020 | Genkin et al. |
| 10,696,956 B2* | 6/2020 | Fuchs .................. C07K 14/435 |
| 2004/0138156 A1 | 7/2004 | Schneider et al. |
| 2004/0157239 A1 | 8/2004 | Tanuma et al. |
| 2009/0010966 A1 | 1/2009 | Davis et al. |
| 2013/0149749 A1 | 6/2013 | Holliger et al. |
| 2013/0236945 A1 | 9/2013 | Song et al. |
| 2014/0199329 A1 | 7/2014 | Wagner et al. |
| 2016/0251638 A1 | 9/2016 | Posada et al. |
| 2016/0376366 A1 | 12/2016 | Chang et al. |
| 2017/0196945 A1 | 7/2017 | Wagner et al. |
| 2020/0024585 A1 | 1/2020 | Fuchs et al. |

FOREIGN PATENT DOCUMENTS

| | | |
|---|---|---|
| WO | WO-199007572 A1 * | 7/1990 |
| WO | 97/40134 | 10/1997 |
| WO | 2011053982 | 5/2011 |
| WO | 2011131772 | 10/2011 |
| WO | 2015066550 | 5/2015 |
| WO | 2016/118476 | 7/2016 |
| WO | WO-2016139659 A1 * | 9/2016 |
| WO | 2018015474 | 1/2018 |
| WO | 2018064681 | 5/2018 |

(Continued)

OTHER PUBLICATIONS

Whisstock et al. Quaterly Reviews of Biophysics, 2003, "Prediction of protein function from protein sequence and structure", 36(3): 307-340.*
Chica et al., Semi-rational approaches to engineering enzyme activity: combining the benefits of directed evolution and rational design. Curr. Opi. Biotechnol., 2005, vol. 16: 378-384.*
Witkowski et al. Conversion of a beta-ketoacyl synthase to a malonyl decarboxylase by replacement of the active-site cysteine with glutamine, Biochemistry. Sep. 7, 1999;38(36):11643-50.*
Hellebreakers et al. Use of fibrinolytic agents in the prevention of postoperative adhesion formation. Fertility and Sterility (2000), 74(2): 203-212.*
Treutner K H et al, "Prevention of Postoperative Adhesions by Single Intraperitoneal Medication", Journal of Surgical Research, Academic Press Inc., San Diego, CA, US,, vol. 59, No. 6, pp. 764-771.
Hellebrekers et al.: "Use of fibrinolytic agents in the prevention of postoperative adhesion formation", Fertility and Sterility., vol. 74, No. 2, Aug. 1, 2000 (Aug. 1, 2000), pp. 203-212.

(Continued)

*Primary Examiner* — Iqbal H Chowdhury
(74) *Attorney, Agent, or Firm* — Morgan, Lewis & Bockius LLP

(57) ABSTRACT

The present invention relates to the treatment of tissue adhesions, e.g. tissue adhesions that occur after surgical interventions. More specifically, the invention refers to an enzyme having DNAse activity for use in a method of treating or preventing tissue adhesions. The invention also relates to a pharmaceutical composition that comprises an enzyme having DNAse activity for use in a method of treating or preventing tissue adhesions.

10 Claims, 6 Drawing Sheets

Specification includes a Sequence Listing.

(56) References Cited

FOREIGN PATENT DOCUMENTS

| WO | 2018134403 | 7/2018 |
|---|---|---|
| WO | 2018134419 | 7/2018 |

OTHER PUBLICATIONS

European Search Report and Written Opinion for European Application No. 18702439.3, dated Jun. 6, 2020, 9 pages.
Al-Mayouf et al., Loss-of-function variant in DNASE1L3 causes a familial form of systemic lupus erythematosus, Nature Genetics, 2011, vol. 43, No. 12, pp. 1186-1188.
Andersen et al. 2014; Extending serum half-life of albumin by engineering neonatal Fc receptor (FcRn) binding. Journal of Biological Chemistry. 289(19): 13492-13502.
Barnes et al. "Targeting potential drivers of COVID-19: Neutrophil extracellular traps", J. Exp. Med., 2020, vol. 217, pp. 1-7.
Baron et al., Cloning and characterization of an actin-resistant DNase I-like endonuclease secreted by macrophages, 3ene, 1998, vol. 215 pp. 291-301.
Berntsson et al., "Structural insight into DNA binding and oligomerization of the multifunctional Cox protein of bacteriophage P2", Nucleic Acids Research, vol. 42, No. 4, 2014, pp. 2725-2735.
Bruschi et al., Neutrophil extracellular traps (NET) induced by different stimuli: A comparative proteomic analysis, PLOS ONE, 2019, pp. 1-18.
Carbonella et al., An autosomal recessive DNASE1L3-related autoimmune disease with unusual clinical presentation mimicking systemic lupus erythematosus, Lupus, 2017, vol. 26, pp. 768-772.
Hakkim et al., "Impairment of neutrophil extracellular trap degradation is associated with lupus nephritis", PNAS, vol. 107, No. 21, 2010, pp. 9813-9818.
International Search Report and Written Opinion for International Application No. PCT/US2018/047084, dated Feb. 15, 2019, 23 pages.
Jimenez-Alcazar et al., "Host DNases prevent vascular occlusion by neutrophil extracellular traps," Science 358, pp. 1202-1206 (2017).
Keyel, "Dnases in health and disease", Developmental Biology, vol. 429, 2017, pp. 1-11.
Kobayashi et al., "Synchronous Growth of Pichia Pastoris for a High-Rate Production of DNaseI at Microquantities", Department of Chemical Engineering. Toyko Institute of Technology. On-Line No. 833, 2004 pp. 1-6.
Landhuis, "Spider-Man' Immune Response May Promote Severe COVID-19", Sci. Am., 2020, pp. 1-7.
Napirei et al. 2009; Murine serum nucleases—contrasting effects of plasmin and heparin on the activities of DNase1 and DNase1-lie 3 (DNase1 13). FEBS Journal. 276: 1059-1073.
Onuora, "DNASE1L3 prevents anti-DNA responses", Nature Rev. Rheumatol., 2016, vol. 12 No. 437, 1 page.
Özçakar et al., DNASE1L3 Mutations in Hypocomplementemic Urticarial Vasculitis Syndrome, Arthritis & Rheumatism, 2013, vol. 65, No. 8, pp. 2183-2189.
Perini et al., "Topical application of Acheflan on rat skin injury accelerates wound healing: a histopathological, immunohistochemical and biochemical study", BMC Complementary and Alternative Medicine, 2015, vol. 15, No. 203, pp. 1-8.
Piccolo et al., "Intrapleural Tissue Plasminogen Activator and Deoxyribonuclease for Pleural Infection; An Effective and Safe Alternative to Surgery", AnnalsATS, vol. 11, No. 9, 2014, pp. 1419-1425.
Reizis, "Project 3: The role of DNASE1L3 and its DNA substrate in lupus", National Institute of Health (NIH), 2015, 5 pages.
Saito et al., Apoptotic DNA endonuclease (DNase-γ) gene transfer induces cell death accompanying DNA fragmentation in human glioma cells, Journal of Neuro-Oncology, 2003, vol. 63, pp. 25-31.
Shiokawa et al. 1998; Molecular cloning and expression of a cDNA encoding an apoptotic endonuclease DNase gamma. Biochem J. 332: 713-720.
Shiokawa et al. 2003; Identification of two functional nuclear localization signals in DNase gamma and their roles in its apoptotic DNase activity. Biochem. J. 376: 377-381.
Sisirak et al., "Digestion of Chromatin in Apoptotic Cell Microparticles Prevents Autoimmunity", Cell vol. 166, 2016, pp. 88-101.
Wang et al., "Targeting the extracellular scavenger DNASE1L3 on SLE", J Xiangya Med, 2017, 3 pages.
Wilber et al., "Deoxyribonuclease I-like III Is an Inducible Macrophage Barrier to Liposomal Transfection", MolecularTherapy, vol. 6, No. 1, 2002, pp. 35-42.
Brill, et al., "Neutrophil extracellular traps promote deep vein thrombosis in mice", J Thromb Haemost. Jan. 2012; 10(1): 136-144.
Brinkmann, et all., "Neutrophil extracellular traps: Is immunity the second function of chromatin?", J. Cell Biol. vol. 198 No. 5 773-783.
CORDIS_project_628264_en, Degradation of Neutrophil Extracellular Traps and its impact on thrombolysis, https://cordis.europa.eu/project/id/628264, 2016, 3 pages.
Fuchs, et al., "Extracellular DNA traps promote thrombosis," PNAS, 2010, vol. 107, No. 36, pp. 15880-15885.
Fuchs, et al., "NET impact on deep vein thrombosis," Arterioscler Thromb Vase Biol. Aug. 2012; 32(8): 1777-1783.
Koyama, et al., "DNase γ, DNase I, and caspase-activated DNase cooperate to degrade dead cells," Genes to Cells 21, 1150-1163 (2016).
Varjú, et al., Fibrinolysis at the Interface of Thrombosis and Inflammation—The Role of Neutrophil Extracellular Traps, Hungarian Scientific Research Fund, Department of Medical Biochemistry, Semmelweis University, Budapest, Hungary, 2014, p. 1-59.
Boettcher et al. "Therapeutic targeting of extracellular DNA improves the outcome of intestinal ischemic reperfusion injury in neonatal rats," Scientific Reports, Nov. 13, 2017.
Branden et al., "Prediction, Engineering, and -Design of Protein Structures", Introduction to Protein Structure, Garland Publishing Inc., New York, p. 247, 1991.
De Meyer et al. "Extracellular Chromatin Is an Important Mediator of Ischemic Stroke in Mice," Arteriosclerosis, Thrombosis, and Vascular Biology, May 24, 2012 (May 24, 2012), vol. 32, No. 8, pp. 1884-1891. entire document.
Parsiegla et al., The Structure of Human DNase I Bound to Magnesium and Phosphate Ions Points to a Catalytic Mechanism Common to Members of the DNase I-like Superfamily, Biochemistry, 2012, vol. 51, pp. 10250-10258.
Rodriguez et al., Gen Bank accession No. 013609 Sep. 27, 2017.
Sadowski et al., "The sequence-structure relationship and protein function prediction", Current Opinion in Structural Biology 19:357-362, 2009.
Seffernick, et al., "Melamine deaminase and Atrazine Chlorohydrolase: 98 Percent Identical but Functionally Different", Journal of Bacteriology, 2001, pp. 2405-2410.
Shiokawa et al., "Characterization of Human DNase I Family Endonucleases and Activation of DNase γ during Apoptosis", Biochemistry 2001, 40, pp. 143-152.
Tang et al., "Identification of Dehalobacter Reductive Dehalogenases that Catalyse Dechlorination of Chloroform, 1,1,1-trichloroethane and 1,1-dichloroethane", Phil Trans R Soc B, 368, 20120318, 1-10, 2013.
Bassi et al. 2012; Regenerative therapies for diabetic microangiopathy. Experimental Diabetes Research. Article ID 916560, pp. 1-11.
Hattori et al. 2018; Nucleic-acid based gene therapy approaches for sepsis. European Journal of Pharmacology. 833: 403-410.

\* cited by examiner

```
Leu Lys Ile Ala Ala Phe Asn Ile Gln Thr Phe Gly Glu Thr Lys Met
1             5                 10                      15

Ser Asn Ala Thr Leu Val Ser Tyr Ile Val Gln Ile Leu Ser Arg Tyr
            20              25                  30

Asp Ile Ala Leu Val Gln Glu Val Arg Asp Ser His Leu Thr Ala Val
        35              40              45

Gly Lys Leu Leu Asp Asn Leu Asn Gln Asp Ala Pro Asp Thr Tyr His
    50              55              60

Tyr Val Val Ser Glu Pro Leu Gly Arg Asn Ser Tyr Lys Glu Arg Tyr
65              70              75                      80

Leu Phe Val Tyr Arg Pro Asp Gln Val Ser Ala Val Asp Ser Tyr Tyr
            85              90                      95

Tyr Asp Asp Gly Cys Glu Pro Cys Gly Asn Asp Thr Phe Asn Arg Glu
            100             105             110

Pro Ala Ile Val Arg Phe Phe Ser Arg Phe Thr Glu Val Arg Glu Phe
        115             120             125

Ala Ile Val Pro Leu His Ala Ala Pro Gly Asp Ala Val Ala Glu Ile
        130             135             140

Asp Ala Leu Tyr Asp Val Tyr Leu Asp Val Gln Glu Lys Trp Gly Leu
145             150             155             160

Glu Asp Val Met Leu Met Gly Asp Phe Asn Ala Gly Cys Ser Tyr Val
                165             170             175

Arg Pro Ser Gln Trp Ser Ser Ile Arg Leu Trp Thr Ser Pro Thr Phe
            180             185             190

Gln Trp Leu Ile Pro Asp Ser Ala Asp Thr Thr Ala Thr Pro Thr His
        195             200             205

Cys Ala Tyr Asp Arg Ile Val Val Ala Gly Met Leu Leu Arg Gly Ala
        210             215             220

Val Val Pro Asp Ser Ala Leu Pro Phe Asn Phe Gln Ala Ala Tyr Gly
225             230             235             240

Leu Ser Asp Gln Leu Ala Gln Ala Ile Ser Asp His Tyr Pro Val Glu
            245             250             255

Val Met Leu Lys
            260
```

Fig. 5

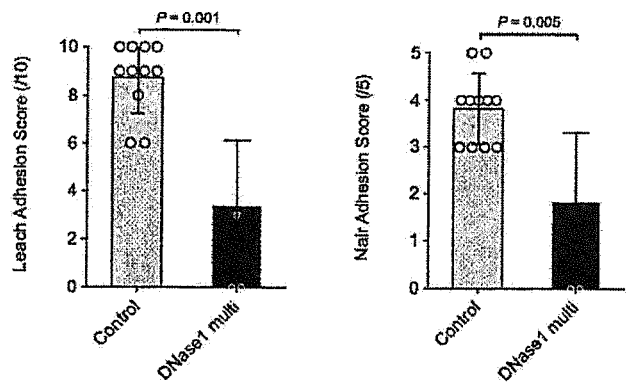
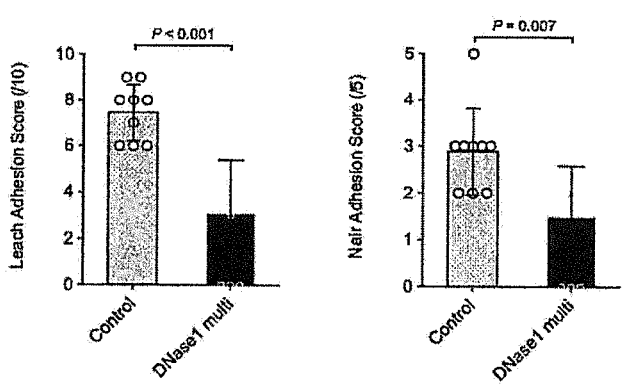
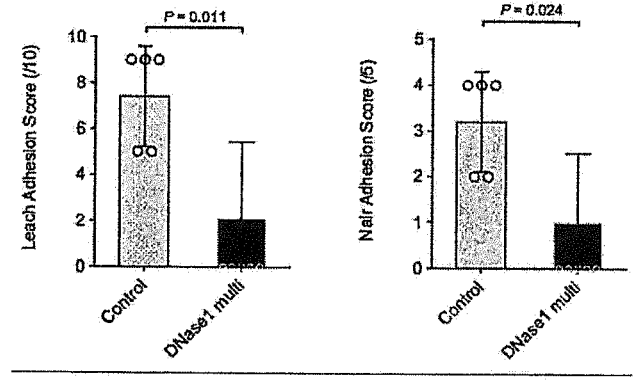
Fig. 6

SEQUENCE LISTING

```
<160> NUMBER OF SEQ ID NOS: 8

<210> SEQ ID NO 1
<211> LENGTH: 282
<212> TYPE: PRT
<213> ORGANISM: Homo sapiens

<400> SEQUENCE: 1

Met Arg Gly Met Lys Leu Leu Gly Ala Leu Leu Ala Leu Ala Ala Leu
1               5                   10                  15

Leu Gln Gly Ala Val Ser Leu Lys Ile Ala Ala Phe Asn Ile Gln Thr
            20                  25                  30

Phe Gly Glu Thr Lys Met Ser Asn Ala Thr Leu Val Ser Tyr Ile Val
        35                  40                  45

Gln Ile Leu Ser Arg Tyr Asp Ile Ala Leu Val Gln Glu Val Arg Asp
    50                  55                  60

Ser His Leu Thr Ala Val Gly Lys Leu Leu Asp Asn Leu Asn Gln Asp
65                  70                  75                  80

Ala Pro Asp Thr Tyr His Tyr Val Val Ser Glu Pro Leu Gly Arg Asn
                85                  90                  95

Ser Tyr Lys Glu Arg Tyr Leu Phe Val Tyr Arg Pro Asp Gln Val Ser
            100                 105                 110

Ala Val Asp Ser Tyr Tyr Tyr Asp Asp Gly Cys Glu Pro Cys Gly Asn
        115                 120                 125

Asp Thr Phe Asn Arg Glu Pro Ala Ile Val Arg Phe Phe Ser Arg Phe
    130                 135                 140

Thr Glu Val Arg Glu Phe Ala Ile Val Pro Leu His Ala Ala Pro Gly
145                 150                 155                 160

Asp Ala Val Ala Glu Ile Asp Ala Leu Tyr Asp Val Tyr Leu Asp Val
                165                 170                 175

Gln Glu Lys Trp Gly Leu Glu Asp Val Met Leu Met Gly Asp Phe Asn
            180                 185                 190

Ala Gly Cys Ser Tyr Val Arg Pro Ser Gln Trp Ser Ser Ile Arg Leu
```

```
            195                 200                 205
Trp Thr Ser Pro Thr Phe Gln Trp Leu Ile Pro Asp Ser Ala Asp Thr
210                 215                 220

Thr Ala Thr Pro Thr His Cys Ala Tyr Asp Arg Ile Val Val Ala Gly
225                 230                 235                 240

Met Leu Leu Arg Gly Ala Val Val Pro Asp Ser Ala Leu Pro Phe Asn
                245                 250                 255

Phe Gln Ala Ala Tyr Gly Leu Ser Asp Gln Leu Ala Gln Ala Ile Ser
            260                 265                 270

Asp His Tyr Pro Val Glu Val Met Leu Lys
            275                 280

<210> SEQ ID NO 2
<211> LENGTH: 305
<212> TYPE: PRT
<213> ORGANISM: Homo sapiens

<400> SEQUENCE: 2

Met Ser Arg Glu Leu Ala Pro Leu Leu Leu Leu Leu Leu Ser Ile His
1               5                   10                  15

Ser Ala Leu Ala Met Arg Ile Cys Ser Phe Asn Val Arg Ser Phe Gly
                20                  25                  30

Glu Ser Lys Gln Glu Asp Lys Asn Ala Met Asp Val Ile Val Lys Val
            35                  40                  45

Ile Lys Arg Cys Asp Ile Ile Leu Val Met Glu Ile Lys Asp Ser Asn
        50                  55                  60

Asn Arg Ile Cys Pro Ile Leu Met Glu Lys Leu Asn Arg Asn Ser Arg
65                  70                  75                  80

Arg Gly Ile Thr Tyr Asn Tyr Val Ile Ser Ser Arg Leu Gly Arg Asn
                85                  90                  95

Thr Tyr Lys Glu Gln Tyr Ala Phe Leu Tyr Lys Glu Lys Leu Val Ser
            100                 105                 110

Val Lys Arg Ser Tyr His Tyr His Asp Tyr Gln Asp Gly Asp Ala Asp
        115                 120                 125

Val Phe Ser Arg Glu Pro Phe Val Val Trp Phe Gln Ser Pro His Thr
130                 135                 140

Ala Val Lys Asp Phe Val Ile Ile Pro Leu His Thr Thr Pro Glu Thr
145                 150                 155                 160

Ser Val Lys Glu Ile Asp Glu Leu Val Glu Val Tyr Thr Asp Val Lys
                165                 170                 175

His Arg Trp Lys Ala Glu Asn Phe Ile Phe Met Gly Asp Phe Asn Ala
            180                 185                 190

Gly Cys Ser Tyr Val Pro Lys Lys Ala Trp Lys Asn Ile Arg Leu Arg
        195                 200                 205

Thr Asp Pro Arg Phe Val Trp Leu Ile Gly Asp Gln Glu Asp Thr Thr
210                 215                 220

Val Lys Lys Ser Thr Asn Cys Ala Tyr Asp Arg Ile Val Leu Arg Gly
225                 230                 235                 240

Gln Glu Ile Val Ser Ser Val Val Pro Lys Ser Asn Ser Val Phe Asp
                245                 250                 255

Phe Gln Lys Ala Tyr Lys Leu Thr Glu Glu Ala Leu Asp Val Ser
            260                 265                 270

Asp His Phe Pro Val Glu Phe Lys Leu Gln Ser Ser Arg Ala Phe Thr
            275                 280                 285
```

Asn Ser Lys Lys Ser Val Thr Leu Arg Lys Lys Thr Lys Ser Lys Arg
    290                 295                 300

Ser
305

<210> SEQ ID NO 3
<211> LENGTH: 299
<212> TYPE: PRT
<213> ORGANISM: Homo sapiens

<400> SEQUENCE: 3

Met Gly Gly Pro Arg Ala Leu Leu Ala Leu Trp Ala Leu Glu Ala
1               5                   10                  15

Ala Gly Thr Ala Ala Leu Arg Ile Gly Ala Phe Asn Ile Gln Ser Phe
            20                  25                  30

Gly Asp Ser Lys Val Ser Asp Pro Ala Cys Gly Ser Ile Ile Ala Lys
        35                  40                  45

Ile Leu Ala Gly Tyr Asp Leu Ala Leu Val Gln Glu Val Arg Asp Pro
    50                  55                  60

Asp Leu Ser Ala Val Ser Ala Leu Met Glu Gln Ile Asn Ser Val Ser
65                  70                  75                  80

Glu His Glu Tyr Ser Phe Val Ser Ser Gln Pro Leu Gly Arg Asp Gln
                85                  90                  95

Tyr Lys Glu Met Tyr Leu Phe Val Tyr Arg Lys Asp Ala Val Ser Val
            100                 105                 110

Val Asp Thr Tyr Leu Tyr Pro Asp Pro Glu Asp Val Phe Ser Arg Glu
        115                 120                 125

Pro Phe Val Val Lys Phe Ser Ala Pro Gly Thr Gly Glu Arg Ala Pro
    130                 135                 140

Pro Leu Pro Ser Arg Arg Ala Leu Thr Pro Pro Leu Pro Ala Ala
145                 150                 155                 160

Ala Gln Asn Leu Val Leu Ile Pro Leu His Ala Ala Pro His Gln Ala
                165                 170                 175

Val Ala Glu Ile Asp Ala Leu Tyr Asp Val Tyr Leu Asp Val Ile Asp
            180                 185                 190

Lys Trp Gly Thr Asp Asp Met Leu Phe Leu Gly Asp Phe Asn Ala Asp
        195                 200                 205

Cys Ser Tyr Val Arg Ala Gln Asp Trp Ala Ala Ile Arg Leu Arg Ser
    210                 215                 220

Ser Glu Val Phe Lys Trp Leu Ile Pro Asp Ser Ala Asp Thr Thr Val
225                 230                 235                 240

Gly Asn Ser Asp Cys Ala Tyr Asp Arg Ile Val Ala Cys Gly Ala Arg
                245                 250                 255

Leu Arg Arg Ser Leu Lys Pro Gln Ser Ala Thr Val His Asp Phe Gln
            260                 265                 270

Glu Glu Phe Gly Leu Asp Gln Thr Gln Ala Leu Ala Ile Ser Asp His
        275                 280                 285

Phe Pro Val Glu Val Thr Leu Lys Phe His Arg
    290                 295

<210> SEQ ID NO 4
<211> LENGTH: 302
<212> TYPE: PRT
<213> ORGANISM: Homo sapiens

<400> SEQUENCE: 4

```
Met His Tyr Pro Thr Ala Leu Leu Phe Leu Ile Leu Ala Asn Gly Ala
1               5                   10                  15

Gln Ala Phe Arg Ile Cys Ala Phe Asn Ala Gln Arg Leu Thr Leu Ala
            20                  25                  30

Lys Val Ala Arg Glu Gln Val Met Asp Thr Leu Val Arg Ile Leu Ala
        35                  40                  45

Arg Cys Asp Ile Met Val Leu Gln Glu Val Val Asp Ser Ser Gly Ser
    50                  55                  60

Ala Ile Pro Leu Leu Leu Arg Glu Leu Asn Arg Phe Asp Gly Ser Gly
65                  70                  75                  80

Pro Tyr Ser Thr Leu Ser Ser Pro Gln Leu Gly Arg Ser Thr Tyr Met
                85                  90                  95

Glu Thr Tyr Val Tyr Phe Tyr Arg Ser His Lys Thr Gln Val Leu Ser
            100                 105                 110

Ser Tyr Val Tyr Asn Asp Glu Asp Val Phe Ala Arg Glu Pro Phe
        115                 120                 125

Val Ala Gln Phe Ser Leu Pro Ser Asn Val Leu Pro Ser Leu Val Leu
    130                 135                 140

Val Pro Leu His Thr Thr Pro Lys Ala Val Glu Lys Glu Leu Asn Ala
145                 150                 155                 160

Leu Tyr Asp Val Phe Leu Glu Val Ser Gln His Trp Gln Ser Lys Asp
                165                 170                 175

Val Ile Leu Leu Gly Asp Phe Asn Ala Asp Cys Ala Ser Leu Thr Lys
            180                 185                 190

Lys Arg Leu Asp Lys Leu Glu Leu Arg Thr Glu Pro Gly Phe His Trp
        195                 200                 205

Val Ile Ala Asp Gly Glu Asp Thr Thr Val Arg Ala Ser Thr His Cys
    210                 215                 220

Thr Tyr Asp Arg Val Val Leu His Gly Glu Arg Cys Arg Ser Leu Leu
225                 230                 235                 240

His Thr Ala Ala Ala Phe Asp Phe Pro Thr Ser Phe Gln Leu Thr Glu
                245                 250                 255

Glu Glu Ala Leu Asn Ile Ser Asp His Tyr Pro Val Glu Val Glu Leu
            260                 265                 270

Lys Leu Ser Gln Ala His Ser Val Gln Pro Leu Ser Leu Thr Val Leu
        275                 280                 285

Leu Leu Leu Ser Leu Leu Ser Pro Gln Leu Cys Pro Ala Ala
    290                 295                 300

<210> SEQ ID NO 5
<211> LENGTH: 260
<212> TYPE: PRT
<213> ORGANISM: Homo sapiens

<400> SEQUENCE: 5

Leu Lys Ile Ala Ala Phe Asn Ile Gln Thr Phe Gly Glu Thr Lys Met
1               5                   10                  15

Ser Asn Ala Thr Leu Val Ser Tyr Ile Val Gln Ile Leu Ser Arg Tyr
            20                  25                  30

Asp Ile Ala Leu Val Gln Glu Val Arg Asp Ser His Leu Thr Ala Val
        35                  40                  45

Gly Lys Leu Leu Asp Asn Leu Asn Gln Asp Ala Pro Asp Thr Tyr His
    50                  55                  60

Tyr Val Val Ser Glu Pro Leu Gly Arg Asn Ser Tyr Lys Glu Arg Tyr
65                  70                  75                  80
```

```
Leu Phe Val Tyr Arg Pro Asp Gln Val Ser Ala Val Asp Ser Tyr Tyr
                85                  90                  95

Tyr Asp Asp Gly Cys Glu Pro Cys Gly Asn Asp Thr Phe Asn Arg Glu
            100                 105                 110

Pro Ala Ile Val Arg Phe Phe Ser Arg Phe Thr Glu Val Arg Glu Phe
        115                 120                 125

Ala Ile Val Pro Leu His Ala Ala Pro Gly Asp Ala Val Ala Glu Ile
    130                 135                 140

Asp Ala Leu Tyr Asp Val Tyr Leu Asp Val Gln Glu Lys Trp Gly Leu
145                 150                 155                 160

Glu Asp Val Met Leu Met Gly Asp Phe Asn Ala Gly Cys Ser Tyr Val
                165                 170                 175

Arg Pro Ser Gln Trp Ser Ser Ile Arg Leu Trp Thr Ser Pro Thr Phe
            180                 185                 190

Gln Trp Leu Ile Pro Asp Ser Ala Asp Thr Thr Ala Thr Pro Thr His
        195                 200                 205

Cys Ala Tyr Asp Arg Ile Val Val Ala Gly Met Leu Leu Arg Gly Ala
    210                 215                 220

Val Val Pro Asp Ser Ala Leu Pro Phe Asn Phe Gln Ala Ala Tyr Gly
225                 230                 235                 240

Leu Ser Asp Gln Leu Ala Gln Ala Ile Ser Asp His Tyr Pro Val Glu
                245                 250                 255

Val Met Leu Lys
            260

<210> SEQ ID NO 6
<211> LENGTH: 285
<212> TYPE: PRT
<213> ORGANISM: Homo sapiens

<400> SEQUENCE: 6

Met Arg Ile Cys Ser Phe Asn Val Arg Ser Phe Gly Glu Ser Lys Gln
1               5                   10                  15

Glu Asp Lys Asn Ala Met Asp Val Ile Val Lys Val Ile Lys Arg Cys
            20                  25                  30

Asp Ile Ile Leu Val Met Glu Ile Lys Asp Ser Asn Asn Arg Ile Cys
        35                  40                  45

Pro Ile Leu Met Glu Lys Leu Asn Arg Asn Ser Arg Arg Gly Ile Thr
    50                  55                  60

Tyr Asn Tyr Val Ile Ser Ser Arg Leu Gly Arg Asn Thr Tyr Lys Glu
65                  70                  75                  80

Gln Tyr Ala Phe Leu Tyr Lys Glu Lys Leu Val Ser Val Lys Arg Ser
                85                  90                  95

Tyr His Tyr His Asp Tyr Gln Asp Gly Asp Ala Asp Val Phe Ser Arg
            100                 105                 110

Glu Pro Phe Val Val Trp Phe Gln Ser Pro His Thr Ala Val Lys Asp
        115                 120                 125

Phe Val Ile Ile Pro Leu His Thr Thr Pro Gly Thr Ser Val Lys Glu
    130                 135                 140

Ile Asp Glu Leu Val Glu Val Tyr Thr Asp Val Lys His Arg Trp Lys
145                 150                 155                 160

Ala Glu Asn Phe Ile Phe Met Gly Asp Phe Asn Ala Gly Cys Ser Tyr
                165                 170                 175

Val Pro Lys Lys Ala Trp Lys Asn Ile Arg Leu Arg Thr Asp Pro Arg
```

```
            180                 185                 190
Phe Val Trp Leu Ile Gly Asp Gln Glu Asp Thr Thr Val Lys Lys Ser
            195                 200                 205

Thr Asn Cys Ala Tyr Asp Arg Ile Val Leu Arg Gly Gln Glu Ile Val
        210                 215                 220

Ser Ser Val Val Pro Lys Ser Asn Ser Val Phe Asp Phe Gln Lys Ala
225                 230                 235                 240

Tyr Lys Leu Thr Glu Glu Ala Leu Asp Val Ser Asp His Phe Pro
            245                 250                 255

Val Glu Phe Lys Leu Gln Ser Ser Arg Ala Phe Thr Asn Ser Lys Lys
            260                 265                 270

Ser Val Thr Leu Arg Lys Lys Thr Lys Ser Lys Arg Ser
            275                 280                 285

<210> SEQ ID NO 7
<211> LENGTH: 279
<212> TYPE: PRT
<213> ORGANISM: Homo sapiens

<400> SEQUENCE: 7

Ala Leu Arg Ile Gly Ala Phe Asn Ile Gln Ser Phe Gly Asp Ser Lys
1               5                   10                  15

Val Ser Asp Pro Ala Cys Gly Ser Ile Ile Ala Lys Ile Leu Ala Gly
            20                  25                  30

Tyr Asp Leu Ala Leu Val Gln Glu Val Arg Asp Pro Asp Leu Ser Ala
        35                  40                  45

Val Ser Ala Leu Met Glu Gln Ile Asn Ser Val Ser Glu His Glu Tyr
    50                  55                  60

Ser Phe Val Ser Ser Gln Pro Leu Gly Arg Asp Gln Tyr Lys Glu Met
65                  70                  75                  80

Tyr Leu Phe Val Tyr Arg Lys Asp Ala Val Ser Val Asp Thr Tyr
            85                  90                  95

Leu Tyr Pro Asp Pro Glu Asp Val Phe Ser Arg Glu Pro Phe Val Val
            100                 105                 110

Lys Phe Ser Ala Pro Gly Thr Gly Glu Arg Ala Pro Pro Leu Pro Ser
            115                 120                 125

Arg Arg Ala Leu Thr Pro Pro Leu Pro Ala Ala Ala Gln Asn Leu
        130                 135                 140

Val Leu Ile Pro Leu His Ala Ala Pro His Gln Ala Val Ala Glu Ile
145                 150                 155                 160

Asp Ala Leu Tyr Asp Val Tyr Leu Asp Val Ile Asp Lys Trp Gly Thr
            165                 170                 175

Asp Asp Met Leu Phe Leu Gly Asp Phe Asn Ala Asp Cys Ser Tyr Val
            180                 185                 190

Arg Ala Gln Asp Trp Ala Ala Ile Arg Leu Arg Ser Ser Glu Val Phe
            195                 200                 205

Lys Trp Leu Ile Pro Asp Ser Ala Asp Thr Thr Val Gly Asn Ser Asp
            210                 215                 220

Cys Ala Tyr Asp Arg Ile Val Ala Cys Gly Ala Arg Leu Arg Arg Ser
225                 230                 235                 240
```

```
Leu Lys Pro Gln Ser Ala Thr Val His Asp Phe Gln Glu Glu Phe Gly
            245                 250                 255

Leu Asp Gln Thr Gln Ala Leu Ala Ile Ser Asp His Phe Pro Val Glu
            260                 265                 270

Val Thr Leu Lys Phe His Arg
        275

<210> SEQ ID NO 8
<211> LENGTH: 284
<212> TYPE: PRT
<213> ORGANISM: Homo sapiens

<400> SEQUENCE: 8

Phe Arg Ile Cys Ala Phe Asn Ala Gln Arg Leu Thr Leu Ala Lys Val
1               5                   10                  15

Ala Arg Glu Gln Val Met Asp Thr Leu Val Arg Ile Leu Ala Arg Cys
            20                  25                  30

Asp Ile Met Val Leu Gln Glu Val Val Asp Ser Ser Gly Ser Ala Ile
        35                  40                  45

Pro Leu Leu Leu Arg Glu Leu Asn Arg Phe Asp Gly Ser Gly Pro Tyr
    50                  55                  60

Ser Thr Leu Ser Ser Pro Gln Leu Gly Arg Ser Thr Tyr Met Glu Thr
65                  70                  75                  80

Tyr Val Tyr Phe Tyr Arg Ser His Lys Thr Gln Val Leu Ser Ser Tyr
                85                  90                  95

Val Tyr Asn Asp Glu Asp Asp Val Phe Ala Arg Glu Pro Phe Val Ala
            100                 105                 110

Gln Phe Ser Leu Pro Ser Asn Val Leu Pro Ser Leu Val Leu Val Pro
        115                 120                 125

Leu His Thr Thr Pro Lys Ala Val Glu Lys Glu Leu Asn Ala Leu Tyr
130                 135                 140

Asp Val Phe Leu Glu Val Ser Gln His Trp Gln Ser Lys Asp Val Ile
145                 150                 155                 160

Leu Leu Gly Asp Phe Asn Ala Asp Cys Ala Ser Leu Thr Lys Lys Arg
                165                 170                 175

Leu Asp Lys Leu Glu Leu Arg Thr Glu Pro Gly Phe His Trp Val Ile
            180                 185                 190

Ala Asp Gly Glu Asp Thr Thr Val Arg Ala Ser Thr His Cys Thr Tyr
        195                 200                 205

Asp Arg Val Val Leu His Gly Glu Arg Cys Arg Ser Leu Leu His Thr
    210                 215                 220

Ala Ala Ala Phe Asp Phe Pro Thr Ser Phe Gln Leu Thr Glu Glu Glu
225                 230                 235                 240

Ala Leu Asn Ile Ser Asp His Tyr Pro Val Glu Val Glu Leu Lys Leu
                245                 250                 255

Ser Gln Ala His Ser Val Gln Pro Leu Ser Leu Thr Val Leu Leu Leu
            260                 265                 270

Leu Ser Leu Leu Ser Pro Gln Leu Cys Pro Ala Ala
        275                 280
```

METHODS FOR TREATING OR PREVENTING TISSUE ADHESIONS

The present invention relates to the treatment of tissue adhesions, e.g. tissue adhesions that occur after surgical interventions. More specifically, the invention refers to an enzyme having DNAse activity for use in a method of treating or preventing tissue adhesions. The invention also relates to a pharmaceutical composition that comprises an enzyme having DNAse activity for use in a method of treating or preventing tissue adhesions.

FIELD OF THE INVENTION

Tissue adhesions are fibrous bands that form between tissues and organs as a part of the body's natural healing process. They regularly occur during surgical interventions which involve a damage of the peritoneum. In addition, they are known to occur regularly in the course of inflammatory diseases of the abdomen and during endometriosis.

Peritoneal healing after surgery is a complex process involving hemostasis, inflammation, angiogenesis, formation of granulation tissue, extracellular matrix deposition, and tissue remodeling. The most important element of peritoneal healing is inflammation which amongst others involves the migration and activation of neutrophils. Neutrophils migrate to injured tissue area and stay there for 1-2 days. At the same time, the inactivation of tissue plasminogen activator (t-PA) due to the peritoneal injury and the distribution of plasminogen activator inhibitors (PAI) by inflammatory cells lead to a massive production of fibrin which further augments the inflammation reaction. When two tissue surfaces are located adjacent to each other, the fibrin can act as a type of glue that promotes the attachment of the surfaces to each other. If the adhesion is not dissolved quickly after its formation, but is allowed to persist, macrophages, endothelial cells and fibroblasts penetrate into the adhesion, resulting in the deposition of collagen and other matrix components to form a permanent adhesion.

While some adhesions do not cause any evident problems, others prevent muscles or organs from moving freely, sometimes causing organs to become twisted or pulled from their normal positions. In some cases, adhesions cause gynecological conditions, female infertility, chronic abdominal pain, digestive discomfort or intestinal obstruction. Adhesions affect the quality of life of millions of patients that undergo surgery, causing costs of several billions of Euros each year.

At present, the only effective way to treat adhesions is to remove them surgically. However, a surgical intervention to remove adhesions in turn bears the risk of inducing additional adhesions. Accordingly, there is a need for alternative means and methods that can prevent or treat tissue adhesions.

DESCRIPTION OF THE INVENTION

It has now been found that tissue adhesions can be effectively treated or prevented by using an enzyme that comprises a deoxyribonuclease (DNAase) activity. Thus, in a first aspect, the invention relates to an enzyme having DNAse activity for use in a method of treating or preventing tissue adhesion in a subject.

The tissue adhesion to be treated can be any type of tissue adhesion which has been described in the art to cause pathological complications, such as gynecological conditions, female infertility, chronic abdominal pain, digestive discomfort or intestinal obstruction. In a preferred embodiment, the adhesion to be treated in the subject is an adhesion that involves the peritoneum. This means that the adhesion is an adhesion of two tissue surfaces of the peritoneum or an adhesion of at least one peritoneal tissue surface with one or more non-peritoneal tissue surfaces, e.g. with a tissue from an organ.

The adhesion to be treated can be caused by any pathological or non-pathological condition. For example, the adhesion can be an adhesion that is caused by a surgical intervention. This means that the subject to be treated has undergone surgery and developed adhesions as a result from surgery. In a preferred aspect, the surgery involved opening and hence damaging of a serous membrane, such as the peritoneum. In particularly preferred embodiment, the surgery that damages the peritoneum involves intestinal anastomosis. Surgical interventions that are known to cause adhesions and which can therefore benefit from the use of an enzyme having DNase activity include, but are not limited to abdominoplasty, hernioplasty, frenuloplasty, Zplasty, diverticulectomy, frenectomy, hemorrhoidectomy, mastoidectomy, thrombectomy, embolectomy, ganglionectomy, lobectomy, myomectomy, panniculectomy, ureterosigmoidostomy, fistulotomy, laparotomy, myringotomy, sphincterotomy, commissurotomy, abdominal surgery, inguinal hernia surgery, biopsy, brostrom prodedure, cauterization, grafting, hypnosurgery, laparoscopy, Nuss procedure, radiosurgery, breast implantation, mastopexy, breast reconstruction, breast reduction plasty, mammoplasty, lumpectomy, mastectomy, muscle biopsy, amputation, tendon transfer, bursectomy, hemicorporectomy, hemipelvectomy, myotomy, tenotomy, fasciotomy, escharotomy, skin biopsy, skin flaps, muscle flaps, khyphoplasty, mentoplasty, acromioplasty, arthroplasty, rotationplasty, ostectomy, femoral head ostectomy, vertebrectomy, coccygectomy, astragalectomy, corpectomy, facetectomy, laminectomy, hemilaminectomy, synovectomy, discectomy, osteotomy, arthrotomy, laminotomy, foraminotomy, epiphysiodesis, arthrodesis, arthroscopy, ulnar collateral ligament reconstruction, vaginoplasty, clitoroplasty, labiaplasty, tuboplasty, fimbrioplasty, cervicectomy, clitoridectomy, oophorectomy, salpingoophorectomy, salpingectomy, hysterectomy, vaginectomy, vulvectomy, salpingostomy, amniotomy, clitoridotomy, hysterotomy, hymenotomy, episiotomy, symphysiotomy, tubal ligation, tubal reversal, colporrhaphy, cesarean section, hymenorrhaphy, endometrial biopsy, phalloplasty, scrotoplasty, vasectomy, penectomy, orchidectomy, prostatectomy, posthectomy, gonadectomy, vasovasostomy, vasoepididymostomy, circumcision and meatotomy, foreskin restoration, orchiopexy, prostate biopsy, urethroplasty, pyeloplasty, nephrectomy, cystectomy, nephrostomy, ureterostomy, cystostomy (suprapubic cystostomy), urostomy, nephrotomy, nephropexy, urethropexy, lithotripsy, kidney transplantation, renal biopsy, uvulopalatoplasty, palatoplasty, gingivectomy, glossectomy, esophagectomy, gastrectomy, appendectomy, proctocolectomy, colectomy, hepatectomy, cholecystectomy, pancreatectomy, pancreaticoduodenectomy, gastrostomy (percutaneous endoscopic gastrostomy), gastroduodenostomy, gastroenterostomy, ileostomy, jejunostomy, colostomy, cholecystostomy, hepatoportoenterostomy, sigmoidostomy, uvulotomy, myotomy (Heller myotomy), pyloromyotomy, anal sphincterotomy, lateral internal sphincterotomy, vertical banded gastroplasty, gastropexy, colon resection, nissen fundoplication, hernia repair, omentopexy, liver biopsy, tonsillectomy, adenoidectomy, thymectomy, splenectomy, lymphadenectomy, thymus transplantation, spleen transplantation, splenopexy, lymph node biopsy, angioplasty, valvuloplasty, pericardiectomy, endarterectomy, cardiotomy, pericardiotomy, heart transplantation, rhinoplasty, septoplasty, rhinectomy, laryngectomy, pneumonectomy, tracheostomy, sinusotomy, pneumotomy, cricothyroidotomy, cricothyrotomy, bronchotomy, thoracotomy, thyrotomy, tracheotomy, pleurodesis, lung transplantation, otoplasty, stapedectomy, mastoidectomy, auriculectomy, myringotomy, punctoplasty, trabeculoplasty, photorefractive keratectomy, trabeculectomy, iridectomy, vitrectomy, dacryocystorhinostomy, radial keratotomy, Mini Asymmetric Radial Keratotomy (M.A.R.K.), corneal transplantation, ganglionectomy, sympathectomy/endoscopic thoracic sympathectomy, neurectomy, axotomy, vagotomy, nerve biopsy, decompressive craniectomy, hemispherectomy, anterior temporal lobectomy, hypophysectomy, amygdalohippocampectomy, ventriculostomy, craniotomy, pallidotomy, thalamotomy, lobotomy, bilateral cingulotomy, cordotomy, rhizotomy, neurosurgery, psychosurgery, and brain biopsy.

In an alternative aspect, the adhesion is caused by thermal lesions in a serous membrane, in particular the peritoneum. In yet another aspect, the adhesion is caused by an inflammatory disease, i.e. without any surgical intervention. In another preferred aspect, the adhesion is an adhesion observed in connection with endometriosis.

In another preferred embodiment, the treatment does not comprise the administration of plasmin, preferably not within 24, 48 or 72 h after DNAse treatment.

The enzyme used for preventing or treating tissue adhesion according to the invention is an enzyme having DNAse activity. As used herein, a DNAse is an enzyme that catalyzes the hydrolytic cleavage of the phosphodiester linkages in the DNA backbone. This results in the degradation of DNA. Different DNAse enzymes are known in the art which differ in their substrate specificities, mode of actions, and biological functions. For example, while DNaseI is known to catalyze the decomposition of free DNA, the enzymes Dnase-1-like 3, Dnase-1-like 2, and Dnase-1-like 1 catalyze the decomposition of DNA that occurs in the form of nucleosomes. In a preferred aspect, the DNAse to be used in the treatment of adhesions is a human DNAse. In an even more preferred aspect, the DNAse is human DNAse1, human Dnase-1-like 3, human Dnase-1-like 2, or human Dnase-1-like 1.

The sequence of human DNase I and certain variants are thereof are set forth in U.S. Pat. Nos. 5,279,823, 6,348,343 and 6,391,607. The sequence of human DNAse1 is set forth in SEQ ID NO:1. The sequence of human Dnase-1-like 3 is set forth in SEQ ID NO:2, the sequence of human Dnase-1-like 2 is set forth in SEQ ID NO:3, and the sequence of human Dnase-1-like 1 is set forth in SEQ ID NO:4.

The enzymes depicted in SEQ ID NOs:1-4 each comprise an N-terminal signal peptide which, however, does not interfere with their biological activity. For the human DNAse1 enzyme shown in SEQ ID NO:1, the signal peptide ranges from amino acid 1-22, and the mature protein ranges from amino acid 23-282. For the human Dnase-1-like 3 enzyme shown in SEQ ID NO:2, the signal peptide ranges from amino acid 1-20, and the mature protein ranges from amino acid 21-305. For the human Dnase-1-like 2 enzyme shown in SEQ ID NO:3, the signal peptide ranges from amino acid 1-20, and the mature protein ranges from amino acid 21-299. For the human Dnase-1-like 1 enzyme shown in SEQ ID NO:4, the signal peptide ranges from amino acid 1-18, and the mature protein ranges from amino acid 19-302. The mature forms of the enzymes depicted in SEQ ID NOs:1-4 are shown in SEQ ID NOs:5-8, respectively.

Thus, in a particular preferred embodiment, the enzyme having DNAse activity used for treating or preventing tissue adhesion comprises or consists of a sequence as depicted in SEQ ID NOs:1, 2, 3, or 4 or a sequence having at least 80% sequence identity to any of those. In yet another embodiment, the enzyme having DNAse activity used for of treating or preventing tissue adhesion comprises or consists of one of the sequences of SEQ ID NOs:5, 6, 7, or 8 or a sequence having at least 80% sequence identity to any of those.

According to the invention, it is also possible to use variants of one of the enzymes depicted in SEQ ID NOs:1-8 as long as these variants have retained a substantial part of the DNA-degrading activity. For example, if a variant of one of the enzymes set forth in SEQ ID NOs:1-8 is used which includes several amino acid substitutions, care must be taken that these substitutions do not result in a significant loss of activity of the enzyme. The enzymes to be used must be enzymatically active, which means that they have retained at least part of the enzymatic activity of the corresponding DNAse depicted in SEQ ID NOs:1-8. Preferably, the enzyme to be used according to the invention has retained 50%, 60%, 70%, 80%, 90%, 95%, 96%, 97%, 98%, or 99% of the activity of the DNAse of one of SEQ ID NOs:1-8. Methods that allow a comparison of the activity of a variant DNAse with one of the DNAses of SEQ ID NOs:1-8 are within the routine skills of a skilled person and include measuring the degradation of a given amount of DNA after addition of a defined amount of the enzyme under identical conditions.

As indicated above, the enzyme to be used by the invention may comprise or consist of one of the amino acid sequences shown in SEQ ID NOs:1-8. However, the invention is not limited to the use of an enzyme that comprises or consists of one of the amino acid sequences shown in SEQ ID NO:1-8. Instead, also enzymatically active variants of the amino acid sequences of SEQ ID NOs:1-8 may be used, which include sequence differences relative to the amino acid sequences depicted in SEQ ID NOs:1-8. For example, the methods of the invention may be conducted with a Dnase, such as DNAse1, from other species, preferably mammalian species, e.g. with DNAse1 from non-human primates or from other closely related species. Variants of the amino acid sequences of SEQ ID NO:1-8 typically differ from the corresponding sequence of SEQ ID NOs:1-8 by one or more deletions, substitutions or additions of amino acids within the polypeptide of SEQ ID NOs:1-8. Accordingly, one or more amino acids of in an enzyme of SEQ ID NOs:1-8 may be substituted or deleted as long as such modification does not or not significantly impair the DNAse activity of the resulting variant.

Generally, any amino acid residue of the amino acid sequence shown in SEQ ID NOs:1-8 can be replaced by a different amino acid, provided that the resultant variant is still an enzymatically active polypeptide with DNAse activity. In particular, the enzyme sequences depicted in SEQ ID NOs:1-8 may be modified by the substitution of a total of 1, 2, 3, 4, 5, 6, 7, 8, 9, 10, 15, 20, 25, 30, 35, 40, 45 or 50 amino acids, and in some embodiments even in up 55 amino acids of the enzyme depicted in any of SEQ ID NOs:1-8. Preferably, these substitutions are not relevant for the DNAse activity of the enzyme.

It is particularly preferred that substitutions are conservative substitutions, i.e. substitutions of one or more amino acid residues by an amino acid of a similar polarity, which acts as a functional equivalent. Preferably, the amino acid residue used as a substitute is selected from the same group of amino acids as the amino acid residue to be substituted.

For example, a hydrophobic residue can be substituted with another hydrophobic residue, or a polar residue can be substituted with another polar residue having the same charge. Functionally homologous amino acids which may be used for a conservative substitution comprise, for example, non-polar amino acids such as glycine, valine, alanine, isoleucine, leucine, methionine, proline, phenylalanine, and tryptophan. Examples of uncharged polar amino acids comprise serine, threonine, glutamine, asparagine, tyrosine and cysteine. Examples of charged polar (basic) amino acids comprise histidine, arginine and lysine. Examples of charged polar (acidic) amino acids comprise aspartic acid and glutamic acid.

The amino acids which can be used for replacing the respective amino acids in the naturally occurring human DNase enzyme, such as the human DNAse1 enzyme, are generally not limited to specific amino acids. In principle, any other proteinogenic or non-proteinogenic amino acid may be used for substituting the naturally occurring amino acid in the respective position of the enzyme. Preferably, the amino acids found in the original DNase enzyme, such as the human DNAse1 enzyme, can be replaced by any other naturally occurring, proteinogenic amino acid. As used herein, proteinogenic amino acids are those 23 amino acids which are regularly found in naturally occurring polypeptides. Preferably, the amino acids are L-amino acids. However, also D-amino acids may be useful for replacing the amino acids in the original polypeptide according to any of SEQ ID NOs:1-8.

Alternatively, the amino acids used for replacing the amino acids in the naturally occurring DNase enzyme, such as the human DNAse1 enzyme, may be non-proteinogenic amino acids, i.e. amino acids which are not found in naturally occurring polypeptides. These non-proteinogenic amino acids include, for example, α-aminoadipic acid, β-aminoadipic acid, α-aminobutyric acid, α-aminoisobutyric acid, β-alanine, 4-aminobutyric acid, 5-aminovaleric acid, 6-aminohexanoic acid, 8-aminooctanoic acid, 9-aminononanoic acid, 10-aminodecanoic acid, 12-aminododecanoic acid, α-aminosuberic acid, β-cyclohexylalanine, citrulline, dehydroalanine, α-cyclohexylglycine, propargylglycine, pyroglutamic acid, 4-benzoylphenylalanine, δ-hydroxylysine, 4-hydroxyproline, allo-isoleucine, lanthionine (Lan), norleucine, norvaline, ornithine, phenylglycin, pipecolic acid, sarcosine, 1,2,3,4-tetrahydro-isochinoline-3-carboxylic acid, allo-threonine, thiazolidine-4-carboxylic acid, yaminobutyric acid (GABA), iso-cysteine, diaminopropionic acid, 2,4-diaminobutyric acid, 3,4-diaminobutyric acid, biphenyl-alanine and 4-fluoro-phenylalanine. Also included by the term "non-proteinogenic amino acids" are derivatives of the above-mentioned proteinogenic amino acids wherein a side-chain has been modified, for example, by a methylene group, thereby providing e.g. homomethionine, homoserine, homoproline, homothreonine, homotryptophane, homotyrosine, homohistidine and homolysine.

Polypeptides which differ from the sequence depicted in SEQ ID NOs:1-8 by the insertion of one or more additional amino acids are considered variants in the context of the present invention. Such insertions can be made at any position of the polypeptide shown in SEQ ID NOs:1-8. Similarly, variants also include polypeptides in which one or more amino acids have been deleted relative to one of the polypeptides shown in SEQ ID NOs:1-8. In principle, such deletions can be applied to any amino acid position within one of the sequences of SEQ ID NOs:1-8.

According to the invention, the variant of the sequence of any of SEQ ID NO:1-8 shows a high degree of sequence, identity with the corresponding reference sequence. The amino acid identity will be at least about 80%, 85%, 90%, 91%, 92%, 93%, 94%, 95%, 96%, 97%, 98% or 99% when compared in an optimal alignment, for example, by the program BESTFIT using standard parameters. For example, a sequence identity of 90% means that 90% of the amino acids of an analyzed amino acid sequence stretch are identical to the sequence of the reference amino acid sequence depicted in one of SEQ ID NOs:1-8. Methods and computer programs for determining amino acid sequence identity are well known in the art.

Also encompassed by the term "variant" are fragments of one of the DNAse enzymes shown in SEQ ID NO:1-8 as well as enzymatically active fragments of the above-mentioned variants of the DNAses shown in SEQ ID NOs:1-8, provided that these fragments are enzymatically active. Enzymatically active fragments of the sequences shown in SEQ ID NO:1-8 or its variants are polypeptides that differ from the amino acid sequences shown in SEQ ID NO:1-8 or from the respective variant sequence by the absence of one or more amino acids at the N-terminus and/or the C-terminus of the polypeptide. For example, a fragment of the sequence of SEQ ID NO:1 may differ from the sequence of SEQ ID NO:1 by the lack of about 5, 10, 15, 20, 25, 30, 35, 40, 45 or 50 amino acids at the N-terminus and/or the C-terminus, provided that such fragment retains at least a part of the enzymatic activity of the original full-length enzyme depicted in SEQ ID NO:1. Likewise, a fragment of a variant of SEQ ID NO:1 may differ from said variant sequence by the lack of about 5, 10, 15, 20, 25, 30, 35, 40, 45 or 50 amino acids at the N-terminus and/or the C-terminus, provided that the fragment is still enzymatically active.

In a particularly preferred aspect, the enzyme to be used in the methods of the invention is a recombinantly produced enzyme. Methods for producing recombinant polypeptides are well known in the art. Polynucleotides encoding the enzyme may be cloned in an expression vector to provide for recombinant preparations of the DNAse enzyme. Generally, expression vectors are self-replicating DNA or RNA constructs into which a polynucleotide of interest is inserted such that the coding sequence of the polynucleotide is operably linked to suitable regulatory elements which allow for the controlled expression of the coding sequence in a host cell. The specific control elements required for expression of the polynucleotide will depend on the host cell used and may include a transcriptional promoter, an operator, an enhancer to increase the mRNA expression level, a ribosome binding site, and suitable transcription and translation terminators. The promoter can be a constitutive or inducible promoter, such as the promoters from SV40, cytomegalovirus (CMV) or Molony murine leukemia virus (MMLV), and the like. Expression vectors may also contain an origin of replication for the autonomous replication of the vector within a host cell, and one or more selection marker which allow monitoring the transfection into the host cell.

The expression vector may be designed for expressing the recombinant protein in a prokaryotic or eukaryotic host. Preferably, the expression vector will have the capability to stably replicate within the host cell so that the number of the polynucleotide which encodes the enzyme of interest is increased within the cell. It is, however, also possible to use an expression vector which is unable to replicate within the cells and allows only transient expression of the recombinant enzyme. Alternatively, expression vectors may be used which integrate into the genome of the host cell that is transduced or transfected with the expression vector. Various expression vectors are known in the prior art which are suitable for mediating expression of the DNAse enzyme both in prokaryotic or eukaryotic host cells. Methods for introducing the expression vector into a host cell have also been extensively discussed in the literature. A variety of different methods may be used for transducing or transfecting the expression vector of the invention into a host cell, for example, electroporation, microinjection, transformation, transfection, protoplast fusion, microprojectile bombardment and the like.

The host cells used for the expression of the DNAse enzyme may be derived from prokaryotes or from lower or higher eukaryotes. Suitable prokaryotes which can be transduced or transfected with an expression vector encoding the DNAse enzyme include, for example, bacteria like *Bacillus subtilis, Escherichia coli*, and the like. Lower eukaryotes that may be used in the methods of the present invention include yeasts, in particular yeasts of the genus *Saccharomyces*, such as *S. cerevisiae, S. bailii, S. bayanus, S. boulardii, S. carlsbergensis*, of the genus *Pichia*, such as *P. pastoris, P. methanolica, P. stipitis*, or of the genus *Dictyostelium*, such as *D. discoideum*. Higher eukaryotes include animal cell lines, in particular mammalian cell lines, for example cell lines derived from rodents, primates and humans. Useful cell lines for use according to the invention include Chinese hamster ovary (CHO) cell lines, baby rat kidney (BRK) cell lines, Madin Darby canine kidney (MDCK) cell lines, NSO myeloma cells, monkey kidney COS cells, human embryonic kidney 293 cells, and cancer cell lines such as SKBR3 cells, Jurket T cells or HeLa cells.

The host cells of the invention which comprise a polynucleotide encoding the DNAse enzyme of the invention, preferably in the form of an expression vector suitable of directing expression in the respective host cell, may be conveniently used for preparing the recombinant enzyme. Preferably, the expression vector is introduced into the host cell such that the expression of the recombinant DNAse enzyme is effected by propagation of the host cells. After its expression in host cells, the recombinant enzyme can be isolated according to routine protocols and formulated into a pharmaceutical composition for use according to the invention.

The present invention hence also provides a pharmaceutical composition which is useful for treating or preventing tissue adhesions. The preparation of pharmaceutical compositions containing a DNAse enzyme as an active ingredient is well known by those working in the field of pharmaceutics. Typically such compositions are prepared either as powders, liquid solutions, or suspensions. The enzyme can be mixed with excipients which are pharmaceutically acceptable and compatible with the active ingredient and in amounts suitable for use in the patients, such as humans.

The pharmaceutical compositions of the present invention will normally contain a physiologically acceptable carrier together with the enzyme dissolved or dispersed therein as an active ingredient. As used herein, the term "pharmaceutically acceptable carrier" comprises, but is not limited to, water, saline, Ringer's Solutions, dextrose solution, and 5% human serum albumin. Liposome-based carriers and non-aqueous vehicles such as fixed oils may also be used. Further examples of suitable carriers for compositions comprising enzymes are described in standard textbooks, for example, in "Remington's Pharmaceutical Sciences", Mack Pub. Co., New Jersey (1991). In addition to the carrier, the composition may also contain further compounds, such as wetting agents, emulsifying agents, pH buffering agents, stabilizers, dyes and the like, insofar as these compounds do not interfere with the activity of the DMAse enzyme.

The pharmaceutical composition provided by the invention will be formulated to be compatible with the intended route of administration. Different routes of administration are feasible for providing the enzyme to the site where treatment is needed. In a particular simple embodiment, the pharmaceutical composition is used as a washing solution during surgery. In this embodiment, the solution will be used for rinsing the tissue surfaces which have been injured during surgery to suppress the formation of adhesions. The enzyme can be dissolved in a sterile solution and can be applied one or several times during the surgical intervention to the tissue surfaces, e.g. organ surfaces or the peritoneum.

Alternatively, the pharmaceutical composition can be formulated for parenteral administration, for example, by intraperitoneal injection or infusion. Pharmaceutical compositions suitable for injection or infusion normally include sterile aqueous solutions or dispersions and sterile powders for the extemporaneous preparation of sterile injectable solutions or dispersions. The composition must be sterile and should be fluid in order to allow a convenient handling in a syringe. The composition should be stable under the conditions of manufacturing and storage and is preferably preserved against the contaminating action of microorganisms such as bacteria and fungi, for example, by including parabens, chlorobutanol, phenol, ascorbic acid, thimerosal, and the like into the composition. For intravenous administration, suitable carriers may comprise physiological saline, bacteriostatic water, Cremophor EL™ (BASF) or phosphate buffered saline (PBS).

The carrier may also be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prolonged absorption of the injectable compositions can be achieved by including in the composition an agent which delays absorption, for example, aluminum monostearate or gelatin.

Sterile injectable solutions can be prepared by incorporating the enzyme in the required amount in an appropriate solvent with one or a combination of the above-mentioned ingredients followed by filter sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

The pharmaceutical composition according to the invention may be formulated for being administered by continuous infusion, for example, continuous infusion for a period of between 2 and 5 days, more preferably a period of between 1 and 2 days.

In one embodiment, the DNAse enzymes to be administered are combined with carriers that will protect the polypeptides against elimination from the body, such as a controlled release formulation, including microencapsulated delivery systems. Biodegradable, biocompatible polymers can be used, such as ethylene vinyl acetate, polyanhydrides, polyglycolic acid, collagen, polyorthoesters, and polylactic acid. Methods for preparing controlled release formulation are well-known in the art. Furthermore, sustained-release compositions can be prepared. Suitable examples of sustained-release preparations include semipermeable matrices of solid hydrophobic polymers, which matrices are in the form of shaped articles, e.g., films or microcapsules. Examples of sustained-release matrices include polyesters, hydrogels, polylactides, non-degradable ethylene-vinyl acetate, degradable lactic acid-glycolic acid copolymers and the like.

The therapeutic composition of the present invention can include pharmaceutically acceptable salts of the components therein. As used herein, pharmaceutically acceptable salts include acid addition salts (formed with the free amino groups of the polypeptide) that are formed with inorganic acids such as, for example, hydrochloric or phosphoric acids, or such organic acids as acetic acid or tartaric acid and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and the like. Particularly preferred are the salts of TFA and HCl, when used in the preparation of cyclic peptides.

The pharmaceutical compositions of the invention will comprise the DNAse enzyme in a therapeutically effective amount. As used herein, a therapeutically effective amount means that the enzyme has to be present in an amount that is sufficient for effectively preventing a tissue adhesion in a subject compared to a control which does not receive any DNAse enzyme. It will be appreciated by those skilled in the art that the concrete amount of the enzyme which is administered to the subject will depend on several factors, such as body weight of the patient, activity of the enzyme, and the cause of tissue adhesion. Generally, where a surgical intervention is suspected to result in tissue adhesion, the amount of DNAse will be selected in consideration of the size of tissue damage that results from the intervention.

A therapeutically effective amount of DNAse, in particular any of the DNases depicted in SEQ ID NO:1-8, typically is an amount in the range of between about 0.15 mg per kg body weight of the subject to about 200 mg per kg body weight, and preferably from about 1.0 mg per kg body weight to about 100 mg per kg body weight, used in one or more dose administrations. Thus, according to a preferred embodiment of the invention, the therapeutically effective amount of the DNAse enzyme is from 5 mg per kg body weight to about 50 mg per kg body weight of the patient. Depending on the DNAse used for the treatment, the above amounts of enzyme correspond to the administration of between 1,000 to 10,000 U of the enzyme to the subject, and preferably between 2,000 to 6,000 U of the enzyme.

The pharmaceutical compositions referred to above are used in the same way as described above with regard to the enzyme, i.e. for treating or preventing tissue adhesion in a subject.

In another preferred embodiment, the treatment does not comprise the administration of plasmin.

DESCRIPTION OF THE FIGURES

FIG. 5 shows the amino acid sequence of the mature human DNAse 1 after cleavage of the signal peptide.

FIG. 6 shows adhesion that was induced by (A) deserositation, (B) intestinal anastomosis, and (C) heat treatment accessed by the Leach and Nair adhesion score.

EXAMPLES

Figure 1:
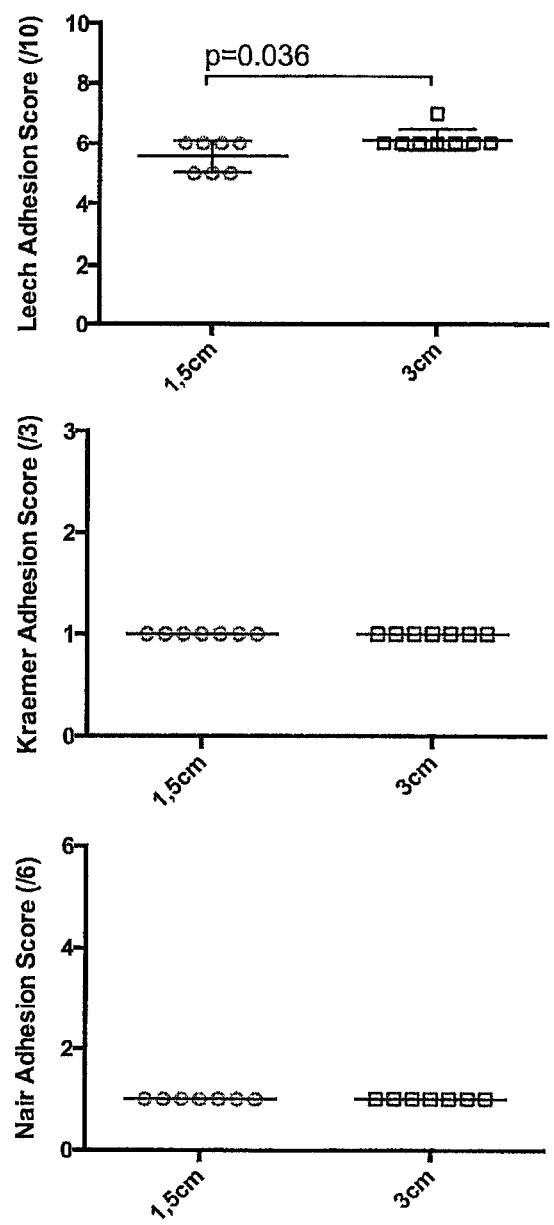
FIG. 1 shows the peritoneal adhesion as measured by the Leach, Kraemer and Nair adhesion score 7 days after making incisions of 1.5 cm and 3 cm, respectively. Differences were calculated by the Mann-Whitney-U-Test.

The experiments referred to below were approved by the Hamburg State Administration for animal research. All environmental parameters within the animal facility were in compliance with the German Law for the Care and Use of Laboratory animals.

Example 1: Induction of Peritoneal Adhesion

The mice were randomly divided into groups comprising the same number of animals. The mice were anesthetized with 5% isoflurane (Baxter, Unterschleißeim, Germany) and maintained with 2.5% isoflurane that was delivered through a facemask. Preoperative antisepsis was performed with betaisadona (Mundipharma GmbH, Limburg, Germany). All mice received 0.02 mg/kg buprenorphine (Reckitt Benckiser, Mannheim, Germany) for analgesia and 10 mg/kg enrofloxacin (Bayer, Leverkusen, Germany) as prophylactic antibiotic therapy subcutaneously.

Adhesions were induced using bipolar electrocoagulation. Standardized lesions were inflicted in an area of 0.5 cm×1.5 cm by sweeping bipolar electrocoagulation forceps over the abdominal peritoneum for 2 seconds. The current was delivered using the following settings: Bipolar Soft, Effect 4, 40 W. The soft coagulation delivers a sinusoidal current of more than 200V ensuring a slow and deep hemostasis without adhering to the tissue.

The defects were subsequently closed using two interrupted sutures (6/0 Vicryl, Ethicon, Norderstedt, Germany) so as to induce an ischemic field around the traumatized area. The sutures were placed equidistantly from each other over the defect (distance: 5 mm). All stitches were made 1 mm from the wound edge. For better standardization, all operations were performed by one operator.

The animals were treated as follows:
  In the controls, only adhesion induction, but no other intervention was performed.
  In the lavage control group, the abdomen of the mice was washed before closure with 1 ml NaCl 0.9%.
  In the lavage group, the abdomen of the mice was washed before closure with 1 ml NaCl 0.9% comprising 10 mg/kg bodyweight DNaseI (Pulmozyme, Roche, Grenzach, Germany).
  In the DNaseI control group, 100 µl NaCl 0.9% was injected i.p. after closure every 24 hours for three days.

In the DNaseI group, 10 mg/kg bodyweight DNaseI (Pulmozyme, Roche, Grenzach, Germany) was injected i.p. after closure every 24 hours for three days.

The abdomen war closed using a 6x0 Ethilon (Ethicon Norderstedt, Germany) running suture.

Example 2: Induction of Adhesion by Deserositation

The mice were randomly divided into groups comprising the same number of animals. The mice were anesthetized with 5% isoflurane (Baxter, Unterschleißheim, Germany) and maintained with 2.5% isoflurane that was delivered through a facemask. Preoperative antisepsis was performed with betaisadona (Mundipharma GmbH, Limburg, Germany). All mice received 0.02 mg/kg buprenorphine (Reckitt Benckiser, Mannheim, Germany) for analgesia subcutaneously. Deserositation was induced by rubbing a mini-prep on the small intestinal wall (distal ileum). No further manipulation was performed.

The animals were treated as follows:
In the controls, only adhesion induction, but no other intervention was performed.
In the DNaseI multi group, the abdomen of the mice was washed before closure with 1 ml NaCl 0.9% comprising 10 mg/kg bodyweight DNaseI (Pulmozyme, Roche, Grenzach, Germany). Additionally, 100 µl NaCl 0.9% was injected i.p. after 24 and 48 hours.

The abdomen war closed using a 6x0 Ethilon (Ethicon Norderstedt, Germany) running suture.

Example 3: Induction of Adhesion by Intestinal Anastomosis

The mice were randomly divided into groups comprising the same number of animals. The mice were anesthetized with 5% isoflurane (Baxter, Unterschleißheim, Germany) and maintained with 2.5% isoflurane that was delivered through a facemask. Preoperative antisepsis was performed with betaisadona (Mundipharma GmbH, Limburg, Germany). All mice received 0.02 mg/kg buprenorphine (Reckitt Benckiser, Mannheim, Germany) for analgesia subcutaneously. Intestinal anastomosis was performed with 8x0 Vicryl (Ethicon Norderstedt, Germany) continuous suture after dissection of the small intestine (distal ileum).

The animals were treated as follows:
In the controls, only adhesion induction, but no other intervention was performed.
In the DNaseI multi group, the abdomen of the mice was washed before closure with 1 ml NaCl 0.9% comprising 10 mg/kg bodyweight DNaseI (Pulmozyme, Roche, Grenzach, Germany). Additionally, 100 µl NaCl 0.9% was injected i.p. after 24 and 48 hours.

The abdomen war closed using a 6x0 Ethilon (Ethicon Norderstedt, Germany) running suture.

Example 4: Induction of Adhesion by Heat Treatment

The mice were randomly divided into groups comprising the same number of animals. The mice were anesthetized with 5% isoflurane (Baxter, Unterschleißheim, Germany) and maintained with 2.5% isoflurane that was delivered through a facemask. Preoperative antisepsis was performed with betaisadona (Nundipharma GmbH, Limburg, Germany). All mice received 0.02 mg/kg buprenorphine (Reckitt Benckiser, Mannheim, Germany) for analgesia subcutaneously.

After median laparotomy the thermic lesions were induced by heat exposure after the viscera (especially the intestine) using a red lamp with a distance of 1 meter for 10 minutes. No further manipulation was performed.

The animals were treated as follows:
In the controls, only adhesion induction, but no other intervention was performed.
In the DNaseI multi group, the abdomen of the mice was washed before closure with 1 ml NaCl 0.9% comprising 10 mg/kg bodyweight DNaseI (Pulmozyme, Roche, Grenzach, Germany). Additionally, 100 µl NaCl 0.9% was injected i.p. after 24 and 48 hours.

The abdomen war closed using a 6x0 Ethilon (Ethicon Norderstedt, Germany) running suture.

Example 5: Adhesion Assessment

All adhesions induced in Example 1-4 were evaluated after relaparotomy and immediately documented with digital photography in a standardized fashion for later blinded evaluation. Macroscopic grading was assessed by two surgeons using the modification tool of Leach grade and Nair grade (Leach et al. (1998), Fertil. Steril. 69: 415-8; Nair et al. (1974), Arch. Surg. 108: 849-53). The Leach grade was originally designed to score adhesion to the uterine horn and was thus modified to evaluate peritoneal adhesions. The Leach score consists of three factors: severity of adhesion (0=no adhesion, 1=filmy avascular, 2=vascular or opaque, 3=cohesive attachment), degree of adhesion (0=no adhesion, 1=adhesion separated with gentle traction, 2=adhesion separated with moderate traction, 3=requiring sharp dissection) and extent of adhesion (0=no adhesion, 1=1-25%, 2=26-50%, 3=51-75%, =76-100%). See Leach et al. (1998), Fertil. Steril. 69: 415–8; Nair et al. (1974), Arch. Surg. 108: 849-53.

Moreover, the Kraemer grade was accessed (Kraemer et al. (2014), Biomed Res Int 2014; 435056). The Kraemer grade is used as follows: 0=no adhesion, 1=avascular adhesion, 2=filmy vascular adhesion, 3=dense, vascular adhesion. The adhesion quality was considered "filmy" if the adhesion was see through. Otherwise, it was considered "dense".

The Nair score consist of two factors (Nair et al. (1974), Arch. Surg. 108: 849-53): macroscopic adhesion (0=no adhesion, 1=single band of adhesion between viscera to abdominal wall, 2=two bands wither between viscera to abdominal wall, 3=more than two bands to abdominal wall) and microscopic adhesion (0=no fibrosis, 1=fibrosis with thin collagen bundle, 2=tissue with wider and less vascularized collagen fibrosis, 3=tissue with thick collagen bundle).

Microscopic Assessment

All specimens were washed in PBS and fixed in 10% buffered formalin. The specimens were embedded in paraffin, cut in sections having a thickness of approximately 5 µm, stained by using hematoxylin and eosin (H&E) and examined by light microscopy by a pathologist blinded to the particular animal groups.

All specimens were histologically evaluated. The adhesive fibrous tissue was dissected with the continuity of the transition zone to the macroscopic normal peritoneal wall. All specimens were fixed in buffered formalin (4%) and embedded in Paraffin according to standardized methods. Serial sections were stained with haematoxylin and eosin and evaluated for the grade of adhesion and fibrosis using light microscopy. All evaluations were performed by a single pathologist who was blinded to the methods and groups.

The degree of fibrosis was assessed by the percentage of extent adhesion area, the grade of fibrosis and the fibrosis depth. The extent adhesion area was defined as the percentage of fibrotic area on the most severe adhesion field. The grade of fibrosis was divided into four grades according to the density of collagen fibers (0: none, 1: thin, 2: moderate, 3: thick). The depth of fibrosis was evaluated by penetration depth of fibrosis from serosa to mucosa (0: none, 1: serosa, 2: muscle, 3: submucosa, 4: mucosa). The inflammation degree was evaluated by the number of inflammatory cells (neutrophils, macrophages, lymphocytes, giant cells and mast cell) under the 10 high power fields (HPFs).

Results:

The results of the macroscopic and microscopic evaluation revealed were as follows. In a first series of experiments, the incision breadth and number of threads was evaluated which reliably induces an abdominal adhesion that imposes no significant burden on the animals. FIG. 1 shows that a more homogeneous adhesion was observed with an incision length of 1.5 cm compared to a 3 cm incision. In both cases a Vicryl thread was inserted 0.5 cm from the margin.

Figure 2:
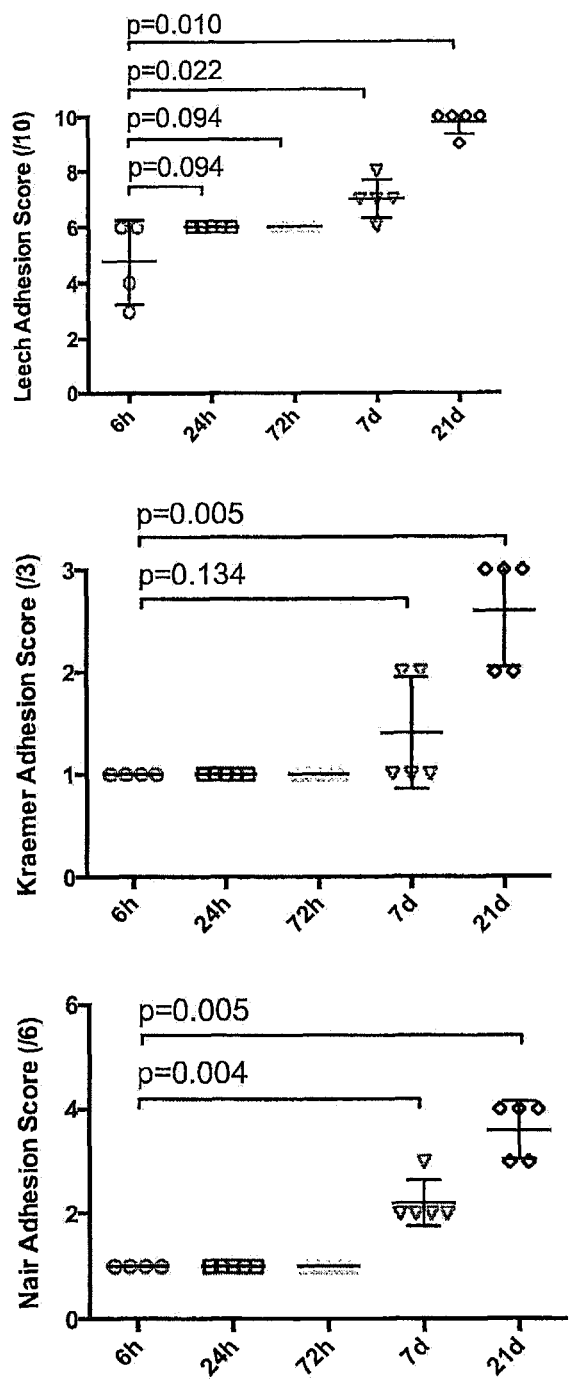
FIG. 2 shows the time course of the peritoneal adhesion as measured by the Leach, Kraemer and Nair adhesion score. Differences were calculated by the Mann-Whitney-U-Test.
Figure 3:
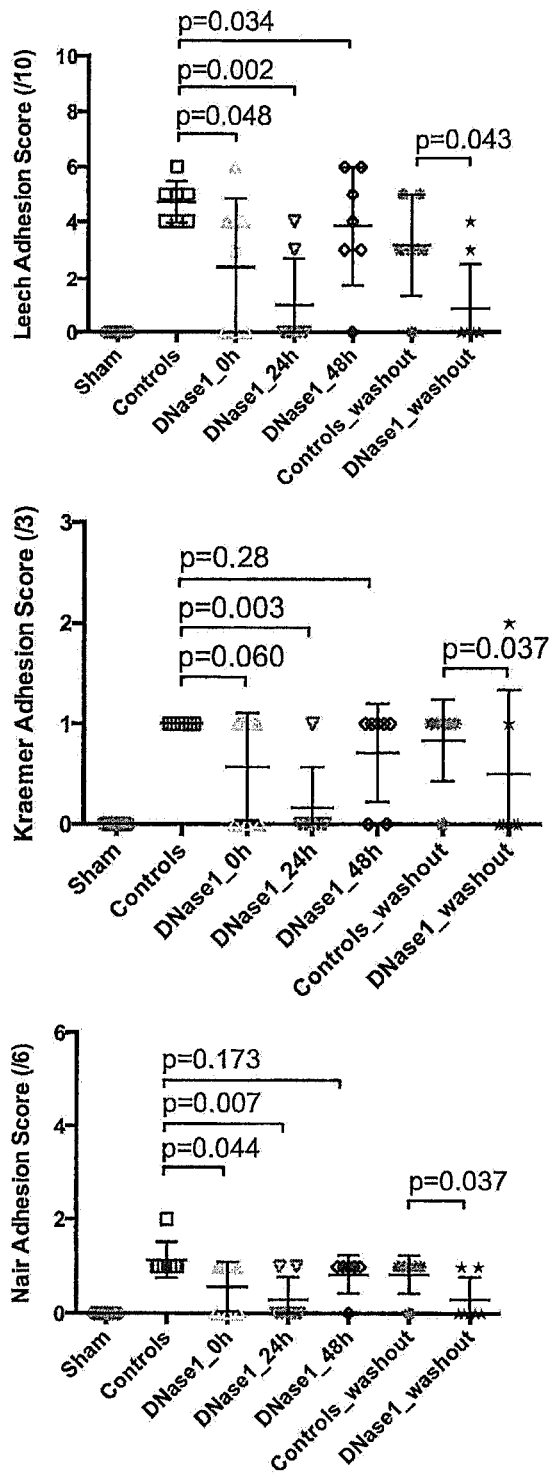
FIG. 3 shows the peritoneal adhesion after 72 hours accessed by the Leach, Kraemer and Nair adhesion score. The figure shows a comparison of the treatment with DNAse1, controls (no treatment) and sham animals (laparotomy only, no peritoneal incision or suture). Differences were calculated by the Mann-Whitney-U-Test.

In a second set of experiments, the time course of adhesion was examined, and the animals were removed from the experiment at different points of time. FIG. 2 depicts shows that adhesions having a score of 5/10 were observed after 6 hours and initially dissolved easily. The adhesions became more distinct with time and increasingly more difficult to dissolve. After 21 days the adhesion reached a maximum.

Figure 4:
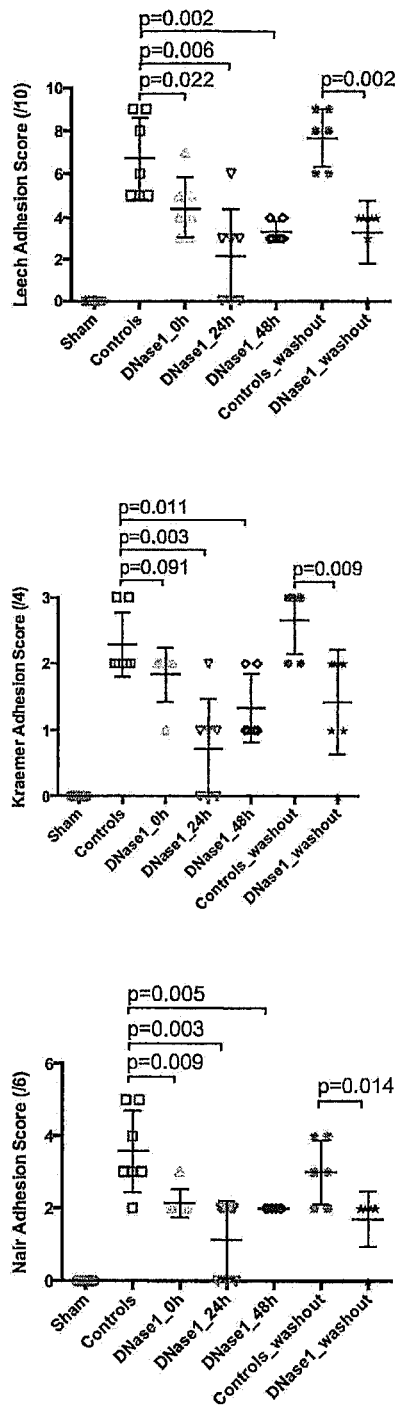
FIG. 4 shows the peritoneal adhesion after 21 days evaluated by the Leach, Kraemer and Nair adhesion score. Differences were calculated by the Mann-Whitney-U-Test.

In a third set of experiments, the systemic or local treatment with DNaseI was examined after 72 hours and 21 days, respectively. As can be seen in FIG. 4, an effective inhibition of the adhesion was achieved both with systemic and local DNaseI. Compared to the control group, all differences were significant.

The results are shown in FIG. 6. As can be seen in FIG. 6A, DnaseI treatment after deserositation significantly reduced adhesion. In addition, DnaseI treatment after deserositation reduced the mortality relative to the control (deserosation 77.8% vs. 70.6%, $p>0.05$).

Similarly, as can be seen in FIG. 6B, DnaseI treatment after intestinal anastomosis significantly reduced adhesion. Compared to a control, the mortality was also significantly reduced by DnaseI treatment (100% vs. 90%, $p>0.05$).

Finally, as shown in FIG. 6C, DnaseI addition after heat treatment likewise reduced adhesion.

What is claimed is:

1. A method of treating or preventing tissue adhesion in a subject undergoing abdominal surgery, comprising administering an enzyme having a deoxyribonuclease (DNase) activity to the subject as a solution one or more times during surgery directly to tissue or organ surfaces injured during the surgery that are at risk of forming adhesions, wherein the enzyme is a human DNase-1-like 3, wherein said human DNase-1-like 3 comprises the amino acid sequence of SEQ ID NO: 6, or a sequence having at least 95% sequence identity thereto, wherein said method does not involve the administration of plasmin.

2. The method of claim 1, wherein said method comprises the administration of between 1,000 to 10,000 Units (U) of the enzyme to the subject.

3. The method of claim 1, wherein said method comprises the administration of the enzyme between 0.15 mg per kg body weight of the subject to 200 mg per kg body weight.

4. The method of claim 1, wherein the enzyme is a recombinantly produced enzyme.

5. The method of claim 1, wherein the surgery is hernia repair.

6. The method of claim 1, wherein the surgery involves intestinal anastomosis.

7. The method of claim 1, wherein the surgery is cesarean section.

8. The method of claim 1, wherein the surgical intervention involves damaging of a serous membrane.

9. The method of claim 8, wherein the serous membrane is a peritoneal membrane.

10. The method of claim 1, wherein the subject suffers from a thermal lesion in a serous membrane.

* * * * *